(12) United States Patent
Kurth et al.

(10) Patent No.: US 10,316,189 B2
(45) Date of Patent: Jun. 11, 2019

(54) POLYMERIZED OILS AND METHODS OF MANUFACTURING THE SAME (71) Applicant: Cargill, Incorporated, Wayzata, MN (US)

(72) Inventors: Todd L. Kurth, Maple Grove, MN (US); Scott Nivens, Minneapolis, MN (US); Christopher Patrick Stevermer, St. Louis Park, MN (US); Hassan Ali Tabatabaee, Plymouth, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/715,665

(22) Filed: Sep. 26, 2017

(65) Prior Publication Data

US 2018/0016438 A1 Jan. 18, 2018

Related U.S. Application Data (62) Division of application No. 15/553,643, filed as application No. PCT/US2016/019767 on Feb. 26, 2016.

(Continued)

(51) Int. Cl.

| C08L 91/00 | (2006.01) |
|---|---|
| C09D 195/00 | (2006.01) |
| C08L 95/00 | (2006.01) |
| E01C 7/26 | (2006.01) |
| E01C 11/00 | (2006.01) |

(Continued)

(52) U.S. Cl.
CPC ............... *C08L 91/00* (2013.01); *C08H 3/00* (2013.01); *C08L 91/02* (2013.01); *C08L 95/00* (2013.01); *C08L 95/005* (2013.01); *C09D 7/65* (2018.01); *C09D 195/00* (2013.01); *E01C 7/26* (2013.01); *E01C 7/262* (2013.01); *E01C 11/005* (2013.01); *C08L 2205/02* (2013.01); *C08L 2205/08* (2013.01); *C08L 2555/28* (2013.01); *C08L 2555/34* (2013.01); *C08L 2555/80* (2013.01);

(Continued)

(58) Field of Classification Search
CPC .......... C08L 75/00; C08L 91/00; C08L 95/00; C08L 2555/28; C09D 195/00; E01C 7/00; E01C 7/262; G01N 25/4866; C11B 3/00; C11C 3/00; C11C 3/006; C10M 129/00; C10M 129/26

See application file for complete search history.

(56) References Cited

U.S. PATENT DOCUMENTS 2,750,298 A 6/1956 Euchner et al.
2,815,296 A 12/1957 Young et al.
(Continued)

FOREIGN PATENT DOCUMENTS

CA 2315955 A1 2/2002
CA 2571214 A1 * 2/2006 ........... C07D 303/42
(Continued)

Primary Examiner — Alexandra M Moore (57) ABSTRACT

Described herein is a polymerized biorenewable, previously modified, or functionalized oil, comprising a polymeric distribution having about 2 to about 80 wt % oligomer content, a polydispersity index ranging from about 1.30 to about 2.20, and sulfur content ranging from 0.001 wt % to about 8 wt %. Methods of manufacturing the polymerized oil as well as its incorporation into asphalt paving, roofing, and coating applications are also described.

25 Claims, 2 Drawing Sheets

Related U.S. Application Data (60) Provisional application No. 62/126,064, filed on Feb. 27, 2015.

(51) Int. Cl.
    *C09D 7/65*     (2018.01)
    *C08H 3/00*     (2006.01)
    *C08L 91/02*     (2006.01)
    *G01N 25/48*     (2006.01)

(52) U.S. Cl.
    CPC ...... *C08L 2555/82* (2013.01); *G01N 25/4866* (2013.01); *Y02A 30/333* (2018.01)

(56) References Cited

U.S. PATENT DOCUMENTS

| | | | |
|---|---|---|---|
| 2,817,653 | A | 12/1957 | Cole et al. |
| 3,595,820 | A | 7/1971 | Den Herder et al. |
| 4,226,552 | A | 10/1980 | Moench |
| 4,740,322 | A | 4/1988 | Dibiase et al. |
| 6,117,227 | A | 9/2000 | Kitagawa |
| 6,133,351 | A | 10/2000 | Hayner |
| 6,956,071 | B2 | 10/2005 | Butler, Jr. et al. |
| 6,987,207 | B1 | 1/2006 | Ronyak |
| 7,951,417 | B1 | 5/2011 | Wen et al. |
| 8,821,064 | B1 | 9/2014 | Morris et al. |
| 2008/0314294 | A1 | 12/2008 | White |
| 2010/0034586 | A1 | 2/2010 | Bailey et al. |
| 2010/0261805 | A1 | 10/2010 | Abraham et al. |
| 2011/0003727 | A1 | 1/2011 | Bloom et al. |
| 2012/0065417 | A1 | 3/2012 | Hora et al. |
| 2012/0315088 | A1 | 12/2012 | Deneuvillers et al. |
| 2013/0184383 | A1 | 7/2013 | Cochran et al. |
| 2014/0083328 | A1 | 3/2014 | Lochel et al. |
| 2014/0261076 | A1 | 9/2014 | Quinn et al. |
| 2014/0338565 | A1 | 11/2014 | Severance et al. |
| 2014/0343192 | A1 | 11/2014 | Cochran et al. |

FOREIGN PATENT DOCUMENTS

| | | | | |
|---|---|---|---|---|
| EP | 0712834 | A1 | 5/1996 | |
| GB | 2462371 | B | 5/2013 | |
| WO | WO-2009137298 | A1 * | 11/2009 | .......... C10M 129/70 |
| WO | 2010016127 | A1 | 2/2010 | |
| WO | 2010077141 | A1 | 7/2010 | |
| WO | WO-2012166414 | A1 * | 12/2012 | ............ C09J 103/02 |
| WO | 2013090283 | A1 | 6/2013 | |
| WO | WO-2013163463 | A1 * | 10/2013 | ............. C08L 91/00 |
| WO | 2015138958 | A1 | 9/2015 | |

\* cited by examiner

POLYMERIZED OILS AND METHODS OF MANUFACTURING THE SAME

CROSS-REFERENCE TO RELATED APPLICATION

This application is a Divisional of U.S. patent application Ser. No. 15/553,643, filed Aug. 25, 2017, entitled "POLYMERIZED OILS & METHODS OF MANUFACTURING THE SAME", which is a national phase application of International Application PCT/US16/019767, filed Feb. 26, 2016, entitled "POLYMERIZED OILS & METHODS OF MANUFACTURING THE SAME", which claims the benefit of U.S. Provisional patent application Ser. No. 62/126,064, filed Feb. 27, 2015, entitled "POLYMERIZED OILS & METHODS OF MANUFACTURING THE SAME", which is hereby incorporated by reference in its entirety.

TECHNICAL FIELD

This disclosure relates to polymerized oils and methods for polymerizing oils and blending with asphalt to enhance performance of virgin asphalt and/or pavements containing recycled and aged bituminous material.

BACKGROUND

Recent technical challenges facing the asphalt industry have created opportunities for the introduction of agriculture-based products for the overall performance enhancement of asphalt. Such performance enhancements may include expanding the useful temperature interval (UTI) of asphalt, rejuvenating aged asphalt, and compatibilizing elastomeric thermoplastic polymers in asphalt.

SUMMARY

Aspects described herein provide a polymerized oil, comprising a polymeric distribution having about 2 to about 80 wt % oligomer content, a polydispersity index ranging from about 1.30 to about 2.20, and sulfur content ranging from 0.001 wt % to about 8 wt %.

Other aspects described herein provide a method of polymerizing an oil comprising heating a biorenewable, previously modified, or functionalized oil to at least 100° C., adding a sulfur-containing compound to the heated oil, and allowing the sulfur-containing compound to react with the oil to produce a polymerized oil comprising a polymeric distribution having about 2 to about 80 oligomer content, a polydispersity index ranging from about 1.30 to about 2.20, and sulfur content ranging from 0.001 wt % to about 8 wt %.

Yet other aspects described herein provide the incorporation of the polymerized oil in asphalt paving, roofing, and coating applications.

DETAILED DESCRIPTION

"Flash Point" or "Flash Point Temperature" is a measure of the minimum temperature at which a material will initially flash with a brief flame. It is measured according to the method of ASTM D-92 using a Cleveland Open Cup and is reported in degrees Celsius (° C.).

"Oligomer" is defined as a polymer having a number average molecular weight (Mn) larger than 1000. A monomer makes up everything else and includes monoacylglycerides (MAG), diacylglycerides (DAG), triacylglycerides (TAG), and free fatty acids (FFA).

"Performance Grade" (PG) is defined as the temperature interval for which a specific asphalt product is designed. For example, in asphalt product designed to accommodate a high temperature of 64° C. and a low temperature of −22° C. has a PG of 64-22. Performance Grade standards are set by America Association of State Highway and Transportation Officials (AASHTO) and the American Society for Testing Materials (ASTM).

"Polydispersity Index" (also known as "Molecular Weight Distribution") is the ratio of weight average molecular weight (Mw) to number average molecular weight (Mn). The polydispersity data is collected using a Gel Permeation Chromatography instrument equipped with a Waters 510 pump and a 410 differential refractometer. Samples are prepared at an approximate 2% concentration in a THF solvent. A flow rate of 1 ml/minute and a temperature of 35° C. are used. The columns consist of a Phenogel 5 micron linear/mixed Guard column, and 300×7.8 mm Phenogel 5 micron columns (styrene-divinylbenzene copolymer) at 50, 100, 1000, and 10000 Angstroms. Molecular weights were determined using the following standards:

| Standard | Monoolein | Diotein | Arcol LHT 240 | Triolein | Epoxidized Soybean Oil | Acclaim 2200 | Multranol 3400 | Acclaim 8200 |
| --- | --- | --- | --- | --- | --- | --- | --- | --- |
| Molecular Weight (Daltons) | 356 | 620 | 707 | 878 | 950 | 2000 | 3000 | 8000 |

"Useful Temperature Interval" (UTI) is defined as the interval between the highest temperature and lowest temperature for which a specific asphalt product is designed. For example, an asphalt product designed to accommodate a high temperature of 64° C. and a low temperature of −22° C. has a UTI of 86. For road paving applications, the seasonal and geographic extremes of temperature will determine the UTI for which an asphalt product must be designed. UTI of asphalt is determined by a series of AASHTO and ASTM standard tests developed by the Strategic Highway Research Program (SHRP) also known as the "Performance Grading" (PG) specification.

Asphalt and Bituminous Materials

For the purpose of this invention asphalt, asphalt binder, and bitumen refer to the binder phase of an asphalt pavement. Bituminous material may refer to a blend of asphalt binder and other material such aggregate or filler. The binder used in this invention may be material acquired from asphalt producing refineries, flux, refinery vacuum tower bottoms, pitch, and other residues of processing of vacuum tower bottoms, as well as oxidized and aged asphalt from recycled bituminous material such as reclaimed asphalt pavement (RAP), and recycled asphalt shingles (RAS).

Starting Oil Material

Biorenewable oils may be used as the starting oil material. Biorenewable oils can include oils isolated from plants, animals, and algae.

Examples of plant-based oils may include but are not limited to soybean oil, linseed oil, canola oil, rapeseed oil, castor oil, tall oil, cottonseed oil, sunflower oil, palm oil, peanut oil, safflower oil, corn oil, corn stillage oil, lecithin (phospholipids) and combinations and crude streams thereof.

Examples of animal-based oils may include but are not limited to animal fat (e.g., lard, tallow) and lecithin (phospholipids), and combinations and crude streams thereof.

Biorenewable oils can also include partially hydrogenated oils, oils with conjugated bonds, and bodied oils wherein a heteroatom is not introduced, for example but not limited to, diacylglycerides, monoacylglycerides, free fatty acids, alkyl esters of fatty acids (e.g., methyl, ethyl, propyl, and butyl esters), diol and triol esters (e.g., ethylene glycol, propylene glycol, butylene glycol trimethylolpropane), and mixtures thereof. An example of biorenewable oils may be waste cooking oil or other used oils.

Previously modified or functionalized oil may also be used as the starting oil material. Examples of previously modified oils are those that have been previously vulcanized or polymerized by other polymerizing technologies, such as maleic anhydride or acrylic acid modified, hydrogenated, dicyclopentadiene modified, conjugated via reaction with iodine, interestified, or processed to modify acid value, hydroxyl number, or other properties. Some examples of previously modified oils are polyol esters, for example polyglycerol ester or a castor oil ester, or estolides. Such modified oils can be blended with unmodified plant-based oils or animal-based oils, fatty acids, glycerin, and/or lecithin. Examples of functionalized oils are those wherein a heteroatom (oxygen, nitrogen, sulfur, and phosphorus) has been introduced.

In preferred aspects, the starting oil material is recovered corn oil (typically residual liquids resulting from the manufacturing process of turning corn into ethanol) (also known as "corn stillage oil") or other low cost waste oils. In another preferred aspect, the starting oil material comprises free fatty acids. One skilled in the art will recognize that if higher functionality is desired, plant-based oils having higher levels of unsaturation may be used.

Sulfur Crosslinking of the Oil

In the various aspects, polymerization of the biorenewable, previously modified, or functionalized oil is achieved through crosslinking of the fatty acid chains and/or the glyceride traction of the tri-glyceride molecules contained in the biorenewable, previously modified, or functionalized oil utilizing a sulfur-containing compound. The sulfur in the sulfur-containing compound is preferably in a reduced form. The polymerization method comprises the steps of (a) heating a biorenewable, previously modified, or functionalized oil (b) adding a sulfur-containing compound to the heated oil, and (c) allowing the sulfur-containing compound to react with the oil to produce a polymerized oil with a desired polymeric distribution (having about 2 wt % to about 80 wt % oligomer content), polydispersity index (from about 1.30 to about 2.20), and sulfur content (between about 0.01 wt % and about 8 wt %).

In a first step, the biorenewable, previously modified, or functionalized oil is heated in a vessel equipped with an agitator to at least 100° C. In more preferred aspects, the biorenewable, previously modified, or functionalized oil (may also be collectively referred to herein as the "oil") is heated to at least 115° C. In preferred aspects, the sulfur-containing compound is gradually added to the heated biorenewable, previously modified, or functionalized oil and may be added in either a solid or a molten form, however it shall be understood that the sulfur-containing compound may be added before the oil or simultaneously with the oil. In preferable aspects, the sulfur-containing compound may be elemental sulfur, but is not limited to such. The reaction between the sulfur and oil inherently increases the temperature of the oil-sulfur mixture and in preferred aspects, the reaction is held at temperatures between about 130° C. and about 250° C., more preferably between about 130° C. and about 220° C., and even more preferably between about 160° C. and about 200° C. during the course of the reaction.

The oil-sulfur mixture may be continuously sparged with a gas-containing stream during the polymerization reaction between the oil and the sulfur. The gas-containing stream may be selected from the group consisting of nitrogen, air, and other gases. The gas-containing stream may help facilitate the reaction and may also assist in reducing odors ($H_2S$ and other sulfides) associated with the reaction, in the final product. Use of air can be beneficial, as it may lead to oxi-polymerization of the oil in addition to the sulfurization process.

Optionally, accelerators may be used to increase the rate of the reaction. Examples of accelerators include, bat are not limited to, zinc oxide, magnesium oxide, dithiocarbamates.

The reaction may continue and may be continuously monitored using gel permeation chromatography (GPC) and/or viscosity until the desired degree of polymerization is achieved as discussed below.

The robustness of the sulfur crosslinking reaction and the ability to use it for the polymerization of lower cost feedstocks containing a high free fatty acid content and residual moisture is an advantage of this polymerization method compared to other processes, providing flexibility in starting material selection.

Polymerization Characteristics

Use reaction between the sulfur-containing compound and the biorenewable, previously modified, or functionalized oil is driven until a polymeric distribution having between about 2 wt % and about 80 wt % oligomers (20 wt % to 98 wt % monomers), and more preferably between about 15 wt % to about 60 wt % oligomers (40 wt % to 85 wt % monomers), and even more preferably between about 20 wt % to about 60 wt % oligomers (40 wt % to 80 wt % monomers) is achieved. In even more preferred aspects, the polymeric distribution ranges from about 50 wt % to about 75 wt % oligomers and about 25 wt % to about 50 wt % monomers.

The polydispersity index of the polymerized oil ranges from about 1.30 to about 2.20, and more preferably from about 1.50 to about 2.05.

A benefit of the reaction described herein is the low sulfur content in the resulting polymerized oil. In some aspects, the sulfur content makes up less than 8 wt % of the polymerized oil. In other aspects, the sulfur content makes up less than 6 wt % of the polymerized oil. In yet other aspects, the sulfur content makes up less than 4 wt % of the polymerized oil. And in other aspects, the sulfur content makes up less than 2 wt % of the polymerized oil. The sulfur content, however, comprises at least 0.001 wt % of the polymerized oil.

The flash point of the resulting polymerized oil, as measured using the Cleveland Open Cup method, is at least about 100° C. and no more than about 400° C. In some aspects, the flash point of the polymerized oil is between about 200° C. and about 350° C. In other aspects, the flash point of the polymerized oil is between about 220° C. and about 300° C. In yet other aspects, the flash point of the polymerized oil is between about 245° C. and about 275° C. The polymerized oils described herein may have higher flash point than its starting oil material, especially when compared against other polymerization techniques.

The viscosity of the polymerized oil will vary based on the type of starting oil material, but generally ranges from about 1 cSt to about 100 cSt at 100° C.

End-Use Applications

In one aspect, the present invention provides a modified asphalt comprising a blend of 60 wt % to 99.9 wt % of asphalt binder and 0.1 wt % to 40 wt % of the polymerized oil, and a method for making the same, in which polymerization of the oil is achieved through sulfur cross-linking as described above. The modified asphalt may be used for road paving or roofing applications.

In another aspect, the present invention provides a modified asphalt comprising a blend of 60 wt % to 99.9 wt % asphalt binder and 0.1 wt % to 40 wt % of the polymerized oil, and a method for making the same, wherein the polymerized oil is a blend of an polymerized oil achieved through sulfur cross-linking, as described above, and one or more of the biorenewable, previously modified or functionalized oils described above, for example: unmodified plant-based oil, animal-based oil, fatty acids, fatty acid methyl esters, gums or lecithin, and gums or lecithin in modified oil or other oil or fatty acid.

Other components, in addition to the polymerized oil, may be combined with an asphalt binder to produce a modified asphalt, for example but not limited to, thermoplastic elastomeric and plastomeric polymers (styrene-butadiene-styrene, ethylene vinyl-acetate, functionalized polyolefins, etc.), polyphosphate acid, anti-stripping additives (amine-based, phosphate-based, etc.), warm mix additives, emulsifiers and/or fibers. Typically, these components are added to the asphalt binder/polymerized oil at doses ranging from about 0.1 wt % to about 10 wt %.

Asphalt Modification

The declining quality of bitumen drives the need for adding chemical modifiers to enhance the quality of asphalt products. Heavy mineral oils from petroleum refining are the most commonly used modifiers. These mineral oils extend the low temperature limit of the asphalt product by 'plasticizing' the binder, however this also tends to lower the upper temperature limit of the asphalt.

Mineral flux oils, petroleum-based crude distillates, and re-refined mineral oils have been used in attempts to soften the asphalt. Often, use of such material results in a decrease of the high temperature modulus of asphalt more than the low temperature, making the asphalt more prone to rutting at high temperatures. Such effects result in the reduction of the Useful Temperature Interval (UTI).

Mineral flux oils, petroleum-based crude distillates, and re-refined mineral oils often have volatile fractions at pavement construction temperatures (e.g., 150 to 180° C.), generally have lower flashpoints than that of asphalt, and may be prone to higher loss of performance due to oxidative aging.

The polymerized oils and blends described herein are not only viable substitute for mineral oil, but have also been shown to extend the UTI of asphalts to a greater degree than other performance modifiers, therefore providing substantial value to asphalt manufacturers. The observed increase in UTI using the polymerized oils described herein is a unique property not seen in other asphalt softening additives such as asphalt flux, fuel oils, or flush oils. Typically one grade improvement in either the SHRP Performance Grading (PG) specification or the Penetration grading system used in many countries is achieved with approximately 2 to 3 wt % of the polymerized oil by weight of the asphalt. For example, the increase in UTI seen for approximately 3% by weight addition of the polymerized oil can be as much as 4° C., therefore providing a broader PG modification range such that the lower end temperature can be lower without sacrificing the higher end temperature.

Rejuvenation of Aged Bituminous Material

Asphalt "ages" through a combination of mechanisms, mainly oxidation and volatilization. Aging increases asphalt modulus, decreases viscous dissipation and stress relaxation, and increases brittleness at lower performance temperatures. As a result, the asphalt becomes more susceptible to cracking and damage accumulation. The increasing usage of recycled and reclaimed bituminous materials which contain highly aged asphalt binder from sources such as reclaimed asphalt pavements (RAP) and recycled asphalt shingles (RAS) have created a necessity for "rejuvenators" capable of partially or completely restoring the theological and fracture properties of the aged asphalt. Aging of asphalt has also been shown to increase colloidal instability and phase incompatibility, by increasing the content of high molecular weight and highly polar insoluble "asphaltene" fraction which may increasingly associate. The use of the polymerized oil described herein are particularly useful for RAP and RAS applications. The polymerized oil described in this document act as a compatibilizer of the asphalt fractions, especially in aged and oxidized asphalt, resulting in a balanced and stable asphalt binder with restored performance and durability.

During plant production the asphalt is exposed to high temperatures (usually between 150 to 190° C.) and exposure to air during which significant oxidation and volatilization of lighter fractions can occur leading to an increase in modulus and a decrease in viscous behavior. The aging process is simulated using a Rolling Thin Film Oven (ASTM D2872) during which a rolling thin film of asphalt is subjected a jet of heated air at about 63° C. for about 85 minutes. The rheological properties are measured before and alter the aging procedure using a Dynamic Shear Rheometer following ASTM D7175 using the ratio of the $|G^*|/\sin \delta$ after to before aging, in which $G^*$ is the complex modulus and $\delta$ is the phase angle. The larger the ratio of the ($|G^*|/\sin \delta$) after aging to the ($|G^*|/\sin \delta$) before aging, the higher the effect of oxidative aging and volatilization on the tested asphalt.

Using this procedure it is shown that asphalts treated with the polymerized oil or blends thereof described in this invention have a lower ratio, thus showing a lower tendency for change in rheological properties as a result of oxidative aging and volatilization.

Accordingly, the polymerized oils described herein have been shown to be capable of rejuvenating aged asphalt binder, and modify the rheological properties of a lesser aged asphalt binder. As a result, small dosages of the polymerized oil can be used to incorporate high content of aged recycled asphalt material into pavements and other applications resulting in significant economic saving and possible reduction in the environmental impact of the pavement through reduction of use of fresh resources.

Elastomeric Thermoplastic Polymer Compatibilization in Asphalt

Asphalt is often modified with thermoplastic elastomeric and plastomeric polymers such as Styrene-Butadiene-Styrene (SBS) to increase high temperature modulus and elasticity, to increase resistance to heavy traffic loading and toughening the asphalt matrix against damage accumulation through repetitive loading. Such polymers are usually used at 3 to 7 wt % dosages in the asphalt and high shear blended into asphalt at temperatures exceeding 180° C. and allowed to "cure" at similar temperatures daring which the polymer swells by adsorption of lighter fractions in the asphalt until a continuous volume phase is achieved in the asphalt.

The volume phase of the fully cured polymer will be affected by degree of compatibility of the polymer in the asphalt, and the fineness of the dispersed particles, resulting in an increased specific area and enhanced swelling potential through increase of the interface surface between asphalt and polymer.

The polymerized oils described in this document have been shown to be capable of further compatibilizing elastomeric polymer in the asphalt when the oil is added and blended into the asphalt before the incorporation of the polymer, or the curing stage. This will be especially effective in asphalt binders that are not very compatible with the elastomeric polymer. Furthermore, the oil may contribute to the lighter fractions that swell the polymers during the curing period.

Warm Mix Additives and Asphalt

In recent years an increasing portion of pavements are produced using what is commonly referred to as "warm mix additives" to produce "warm mix" asphalt pavements. Warm mix pavements can be produced and compacted at lower production temperatures, require less compaction effort to achieve target mixture density, and as a result can retain the properties necessary for compaction at lower temperature enabling an increase in the maximum haul distance of the asphalt mixture from the plant to the job site.

The different mechanisms through which warm mix additives provide a benefit include increased lubrication of aggregates during asphalt mixture compaction, reduction of the binder viscosity at production temperatures, and better coating and wettability of the aggregates. Thus a diverse range of chemicals and additives may exhibit one or more of the properties attributed to warm mix additives when added to an asphalt mixture.

The polymerized oils described herein cars be used as a warm mix additive and/or compaction aid, to achieve a number of the benefits expected from a warm mix additive, including minimum decreasing production and construction temperatures through increase in aggregate lubrication and aggregate wettability. In such an application the additive would be used at dosages preferably in the range of between about 0.1 and 2% by weight of the bitumen.

EXAMPLES

The following examples are presented to illustrate the present invention and to assist one of ordinary skill in making and using same. The examples are not intended in any way to otherwise limit the scope of the invention.

Experimental Method

A charge of precipitated suitor (mass ranges between 65 grams to 56.5 grams) is added to a 1 liter round bottom flask containing 650 grams of vegetable oil. The reactor is then heated to the target reaction temperature using a heating mantle, taking care not to over shoot the target temperature by more than 5° C. The reaction mixture is agitated using a motorized stirrer with a stir shaft and blade. The reaction is continuously sparged with nitrogen at 2-12 standard cubic feet per hour (SCFH). A condenser and receiving flask is used to collect any distillate.

It is noted that the reaction will create foam around 110-115° C. when the sulfur melts into the oil. The reaction is monitored using GPC, to measure the oligomer content and distribution, and viscosity is measured at 40° C. using ASTM D445. The reaction is considered complete when the desired oligomer content has been achieved. The reactor is then cooled to 60° C.

Example 1: Asphalt Modified with Polymerized Palm Oil #1

A modified asphalt binder comprising:

97.0% by weight of neat (i.e., unmodified) asphalt binder graded at a standard grade of PG 64-22 (and "true" grade of PG 64.88-24.7) Note: the true grade represents the exact temperatures at which the asphalt reset the controlling specification values, which will always meet and exceed that of the corresponding standard grade (i.e. the true high temperature grade will always be larger than the standard high temperature grade, and the true low temperature grade will always be lower than that of the standard low temperature grade).

3.0% by weight of sulfurized refined palm oil reacted with 3% by weight of elemental sulfur at 160° C. for 5 hrs under a Nitrogen sparge. This resulted in a modifier with:

31.8% oligomers

Viscosity of 17.2 cSt at 100° C.

Polydispersity Index (PDI) of approximately 1.30

The modifier was blended into the asphalt after the binder had been annealed at 150° C. for 1 hour. Performance grade tests were performed in accordance with AASHTO M320. The modification resulted in a 4.8° C. low temperature grade improvement, taking the neat binder grade of PG 64-22 to a PG 58-28. The net change in the high and low performance grade resulted in a Useful Temperature Interval improved by 0.8° C. Details are shown in Table 1.

TABLE 1

| Binder Name | UTI[1] ° C. | O-DSR[2] ° C. | R-DSR[3] ° C. | S-BBR[4] ° C. | m-BBR[5] ° C. |
|---|---|---|---|---|---|
| Unmodified | 89.6 | 64.88 | 65.88 | −25.8 | −24.7 |
| +3% Sulfurized Refined Palm Oil #1 | 90.4 | 60.04 | 60.72 | −30.4 | −32.7 |

[1]UTI: Useful Temperature Interval, as the difference between the high temperature performance grade and the low temperature performance grade, as determined using AASHTO M320.
[2]O-DSR: The High Temperature Performance Grade of the Unaged ("Original") asphalt binder as measured using a Dynamic Shear Rheometer (DSR) following ASTM D7175 and AASHTO M320.
[3]R-DSR: The High Temperature Performance Grade of the Rolling Thin Film Oven Aged (RTFO, following ASTM D2872) asphalt binder as measured using a Dynamic Shear Rheometer (DSR) following ASTM D7175 and AASHTO M320.
[4]S-BBR: The Low Temperature Performance Grade controlled by the Creep Stiffness parameter ("S"), as measured on an asphalt binder conditioned using both the Rolling Thin Film Oven (ASTM D2872) and Pressure Aging Vessel (ASTM D6521), using a Bending Beam Rheometer following ASTM D6648 and AASHTO M320.
[5]m-BBR: The Low Temperature Performance Grade controlled by the Creep Rate parameter ("in" value), as measured on an asphalt binder conditioned using both the Rolling Thin Film Oven (ASTM D2872) and Pressure Aging Vessel (ASTM D6521), using a Bending Beam Rheometer following ASTM D6648 and AASHTO M320.

Example 2: Asphalt Modified with Polymerized Palm Oil #2

A modified asphalt binding comprising:
97.0% by weight of neat asphalt binder graded as PG 64-22 (true PG 64.88-24.7)
3.0% by weight of sulfurized refined palm oil reacted with 4% by weight of elemental sulfur at 160° C. for 20.5 hrs under a Nitrogen sparge. This resulted in a modifier with:
56.18% oligomers
Viscosity of 25.0 cSt at 100° C.
PDI of approximately 1.50

The modifier was blended into the asphalt after the binder had been annealed at 150° C. for 1 hour. Performance grade tests were performed in accordance to AASHTO M320. The modification resulted in a 5.9° C. low temperature grade improvement, taking the neat binder grade of PG 64-22 to a PG 58-28. The net change in the high and low performance grade resulted in a Useful Temperature Interval improved by 1.5° C. Details are shown in Table 2.

TABLE 2

| Binder Name | UTI ° C. | O-DSR ° C. | R-DSR ° C. | S-BBR ° C. | m-BBR ° C. |
|---|---|---|---|---|---|
| Unmodified | 89.6 | 64.88 | 65.88 | −25.8 | −24.7 |
| +3% Sulfurized Refined Palm Oil #2 | 91.1 | 60.54 | 61.13 | −30.6 | −34.1 |

Example 3: Asphalt Modified with Sulfurized Recovered Corn Oil #1

A modified asphalt binder comprising:
97.0% by weight of neat asphalt binder graded as PG 64-22 (true PG 64.88-24.7)
3.0% by weight of sulfurized recovered corn oil (RCO) reacted with 1.5% by weight of elemental sulfur at 160° C. for 7 hrs under a Nitrogen sparge. This resulted in a modifier with:
16.0% oligomers
PDI of approximately 1.50

The modifier was blended into the asphalt after the binder had been annealed at 150° C. for 1 hour. Performance grade tests were performed in accordance to AASHTO M320. The modification resulted in a 6.0° C. low temperature grade improvement taking the neat binder grade of PG 64-22 to a PG 58-28. The net change in the high and low performance grade resulted in a Useful Temperature Interval improved by 0.4° C. Details are shown in Table 3.

TABLE 3

| Binder Name | UTI ° C. | O-DSR ° C. | R-DSR ° C. | S-BBR ° C. | m-BBR ° C. |
|---|---|---|---|---|---|
| Unmodified | 89.6 | 64.88 | 65.88 | −25.8 | −24.7 |
| +3% Sulfurized RCO 1 | 90.0 | 59.28 | 60.34 | −30.7 | −33.6 |

Example 4: Asphalt Modified with Sulfurized Recovered Corn Oil #2

A modified asphalt binder comprising:
97.0% by weight of neat asphalt binder graded as PG 64-22 (true PG 64.88-24.7)
3.0% by weight of sulfurized recovered corn oil (RCO) reacted with 6.0% by weight of elemental sulfur at 160° C. for 6 hrs under a Nitrogen sparge. This resulted in a modifier with:
50.3% oligomers
Viscosity at 40° C. was 270 cSt
PDI of approximately 2.19

The modifier was blended into the asphalt alter the binder had been annealed at 150° C. for 1 hour. Performance grade tests were performed in accordance to AASHTO M320. The modification resulted in a 4.4° C. low temperature grade improvement, taking the neat binder grade of PG 64-22 to a PG 58-28. The net change in the high and low performance grade resulted in a Useful Temperature Interval improved by 0.7° C. Details are shown in Table 4.

TABLE 4

| Binder Name | UTI ° C. | O-DSR ° C. | R-DSR ° C. | S-BBR ° C. | m-BBR ° C. |
|---|---|---|---|---|---|
| Unmodified | 89.6 | 64.88 | 65.88 | −25.8 | −24.7 |
| +3% Sulfurized RCO 2 | 90.3 | 61.23 | 61.3 | −29.1 | −30.9 |

Example 5: Asphalt Modified with Sulfurized Refined Sunflower Oil Blend #1

A modified asphalt binder comprising:
97.0% by weight of neat asphalt binder graded as PG 64-22 (true PG 64.88-24.7)
3.0% by weight of a blend having:
14.5% by weight of a sulfurized refined sun flower oil reacted with 7.0% by weight of elemental sulfur at 160° C. for 19 hrs under a Nitrogen sparge. This resulted in a modifier with 70.8% oligomers
85.5% by weight of refined sunflower oil
Blend of the sulfurized oil and the unmodified oil had 11.9% oligomer content, a viscosity of 55 cSt at 40° C., and a PDI of approximately 1.64.

The modifier was blended into the asphalt after the binder had been annealed at 150° C. for 1 hour. Performance grade tests were performed in accordance to AASHTO M320. The modification resulted in a 5.3° C. low temperature grade improvement, taking the neat binder grade of PG 64-22 to a PG 58-28. The net change in the high and low performance grade resulted in a full low temperature grade improvement with no change in the Useful Temperature Interval. Details are shown in Table 5.

TABLE 5

| Binder Name | UTI ° C. | O-DSR ° C. | R-DSR ° C. | S-BBR ° C. | m-BBR ° C. |
|---|---|---|---|---|---|
| Unmodified | 89.6 | 64.88 | 65.88 | −25.8 | −24.7 |
| +3% Sulfurized Sun Flower Oil Blend 1 | 89.6 | 59.55 | 60.40 | −30.0 | −30.3 |

Example 6: Asphalt Modified with Sulfurized Refined Sunflower Oil Blend #2

A modified asphalt binder comprising:
97.0% by weight of neat asphalt binder graded as PG 64-22 (true PG 64.88-24.7)
3.0% by weight of a blend having:
53.9% by weight of a sulfurized refined sunflower oil reacted with 7.0% by weight of elemental sulfur at 160° C. for 19 hrs under a Nitrogen sparge. This
resulted in a modifier with 70.8% oligomers
46.1% by weight of refined sunflower oil
Blend of the sulfurized oil and the unmodified oil had
42.76% oligomer content, a viscosity of 177 Cst at
40° C., and a PDI of approximately 3.16.

The modifier was blended into the asphalt after the binder had been annealed at 150° C. for 1 hour. The modification resulted in a 4.8° C. low temperature grade improvement, taking the neat binder grade of PG 64-22 to a PG 58-28. Performance grade tests were performed in accordance to AASHTO M320. The net change in the high and low performance grade resulted in a Useful Temperature Interval improved by 0° C. Details are shown is Table 6.

TABLE 6

| Binder Name | UTI °C. | O-DSR °C. | R-DSR °C. | S-BBR °C. | m-BBR °C. |
|---|---|---|---|---|---|
| Unmodified | 89.6 | 64.88 | 65.88 | −25.8 | −24.7 |
| +3% Sulfurized Sun Flower Oil Blend 2 | 89.7 | 60.24 | 61.25 | −29.5 | −34.2 |

Example 7: Asphalt Modified with Sulfurized Refined Sunflower Oil Blend #3

A modified asphalt binder comprising:
97.0% by weight of neat asphalt binder graded as PG 64-22 (true PG 64.88-24.7)
3.0% by weight of a blend having:
63.4% by weight of a sulfurized refined sunflower oil reacted with 7.0% by weight of elemental sulfur at 160° C. for 19 hrs under a Nitrogen sparge. This resulted in a modifier with 70.8% oligomers
36.6% by weight of refined sunflower oil
Blend of the sulfurized oil and the unmodified oil had 48.3% oligomer content, a viscosity of 254 Cst at 40° C., and a PDI of approximately 3.55.

The modifier was blended into the asphalt after the binder had been annealed at 150° C. for 1 hour. Performance grade tests were performed in accordance to AASHTO M320. The modification resulted in a 5° C. low temperature grade improvement, taking the neat binder grade of PG 64-22 to a PG 58-28. The net change in the high and low performance grade resulted in a Useful Temperature Interval improved by 0° C. Details are shown in Table 5.

TABLE 5

| Binder Name | UTI °C. | O-DSR °C. | R-DSR °C. | S-BBR °C. | m-BBR °C. |
|---|---|---|---|---|---|
| Unmodified | 89.6 | 64.88 | 65.88 | −25.8 | −24.7 |
| +3% Sulfurized Sun Flower Oil Blend 3 | 90.4 | 60.70 | 61.64 | −29.7 | −34.7 |

Example 8: Asphalt Modified with Refined Sunflower Oil Blend with Palm Oil #1

A modified asphalt binder comprising:
97.0% by weight of neat asphalt binder graded as PG 64-22 (true PG 64.88-24.7)
3.0% by weight of a blend having:
14.5% by weight of a sulfurized refined sunflower oil reacted with 7.0% by weight of elemental sulfur at 160° C. for 19 hrs under a Nitrogen sparge. This resulted in a modifier with 70.8% oligomers
84.5% by weighs of palm oil
Blend of the sulfurized oil and the palm oil had about 11.9% oligomer content
PDI of approximately 1.77

Use modifier was blended into the asphalt after the binder had been annealed at 150° C. for 1 hour. Performance grade tests were performed in accordance to AASHTO M320. The modification resulted in a 5° C. low temperature grade improvement, taking the nest binder grade of PG 64-22 to a PG 58-28. The net change in the high and low performance grade resulted in a Useful Temperature Interval slightly decreased by 0.2° C. Details are shown in Table 6.

TABLE 6

| Binder Name | UTI °C. | O-DSR °C. | R-DSR °C. | S-BBR °C. | m-BBR °C. |
|---|---|---|---|---|---|
| Unmodified | 89.6 | 64.88 | 65.88 | −25.8 | −24.7 |
| +3% Sulfurized SFO-Palm Oil Blend 1 | 89.4 | 59.65 | 60.58 | −29.7 | −30.1 |

Example 9: Asphalt Modified with Sulfurized Refined Sunflower Oil Blend with Palm Oil #2

A modified asphalt binder comprising:
97.0% by weight of neat asphalt binder graded as PG 64-22 (true PG 64.88-24.7)
3.0% by weight of a blend having:
59.0% by weight of a sulfurized refined sunflower oil reacted with 7.0% by weight of elemental sulfur at 160° C. for 19 hrs under a Nitrogen sparge. This resulted in a modifier with 70.8% oligomer
41.0% by weight of palm oil
Blend of the sulfurized oil and the palm oil had about 43% oligomer content and a PDI of approximately 2.37

The modifier was blended into the asphalt after the binder had been annealed at 150° C. for 1 hour. Performance grade tests were performed in accordance to AASHTO M320. The modification resulted in a 4.2° C. low temperature grade improvement, taking the neat binder grade of PG 64-22 to a PG 58-28. The net change in the high and low performance grade resulted in a Useful Temperature interval slightly decreased by 0.1° C. Details are shown in Table 7.

TABLE 7

| Binder Name | UTI °C. | O-DSR °C. | R-DSR °C. | S-BBR °C. | m-BBR °C. |
|---|---|---|---|---|---|
| Unmodified | 89.6 | 64.88 | 65.88 | −25.8 | −24.7 |
| +3% Sulfurized SFO-Palm Oil Blend 2 | 89.5 | 60.62 | 61.24 | −28.9 | −33.1 |

Example 10: Asphalt Modified with Sulfurized Soy Acid Oil (Also Known as "Acidulated Soap Stock")

A modified asphalt binder comprising:
97.0% by weight of seat asphalt binder graded as PG 64-22 (true PG 64.88-24.7)
3.0% by weight of a sulfurized refined Soy Acid Oil reacted with 5.0% by weight of elemental sulfur at 160° C. for 8 hrs under a Nitrogen sparge. This resulted in a modifier with 28.14% oligomer, a viscosity of 167 cSt at 40° C., and a PDI of approximately 2.36. The modifier was blended into the asphalt alter the binder had been annealed at 150° C. for 1 hour. Performance grade tests were performed in accordance to AASHTO M320. The modification resulted in a 3.3° C. low temperature grade improvement, taking the neat binder grade of PG 64-22 to a PG 58-28. The net change in the high and low performance grade resulted in a Useful Temperature Interval decreased by 1.5° C. This example highlights the potential undesirable effect of the free fatty acid content on the modifier's performance, as it is significantly less effective in improving the low temperature performance grade compared so the drop caused at the high temperature grade. Details are shown in Table 10.

Performance grade vests were performed in accordance to AASHTO M320. Multiple Stress Creep and Recovery tests were performed on the unaged binder at 76° C. and on the RTFO residue at 64° C. in accordance to AASHTO T350. The results show that despite the reduction in modulus the average percent of recovery of the binder increased for the binder containing the modifier, indicating the effect of the modifier as a compatibilizer of SBS, resulting in a better distribution of the same mass of the elastomeric polymer compared to the binder that did not contain the modifier and consequently a more efficient elastic network. Details are shown in Table 9.

TABLE 9

| Binder Name | DSR |G*|/sinδ Unaged | | | MSCR at 3.2 kPa Recovery at 64° C. (RTFO) | MSCR at 3.2 kPa Recovery at 76° C. (Unaged) |
| --- | --- | --- | --- | --- | --- |
| | 70° C. | 76° C. | 82° C. | (%) | (%) |
| +5.5% SBS + 0.09% Sulfur | 4.05 | 2.51 | 1.62 | 89.0% | 67.7% |
| +2% Example#1 + 5.5% SBS + 0.09% Sulfur | 3.34 | 2.11 | 1.40 | 93.1% | 70.0% |

TABLE 8

| Binder Name | UTI ° C. | O-DSR ° C. | R-DSR ° C. | S-BBR ° C. | m-BBR ° C. |
| --- | --- | --- | --- | --- | --- |
| Unmodified | 89.6 | 64.88 | 65.88 | −25.8 | −24.7 |
| +3% Sulfurized Soy Acid Oil | 88.1 | 60.07 | 61.39 | −28 | −31.6 |

Example 11: Asphalt Modified with StyreneButadieneStyrene and Sulfurized Recovered Corn Oil #1 as a Compatibilizer A modified asphalt binder comprising:
92.41% by weight of neat asphalt binder graded as PG 64-22 (true PG 54.88-24.7)
5.5% by weight of Linear StyreneButadieneStyrene (SBS)
0.09% by weight of Elemental Sulfur (used as an SBS cross linker in the asphalt binder
2.0% by weight of sulfurized recovered corn oil (RCO) as described in Example #3.

Blending Procedure:
1. The modifier was blended into the asphalt after the binder had been annealed at 150° C. for 1 hour. The modified binder heated to about 193° C. for polymer modification.
2. The RPM in the high shear mixer was set to 1000 while the SBS was added (within 1 minute). Immediately after addition of the polymer the RPM was briefly ramped up to 3000 rpm for approximately 10 minutes to insure full break down of the SBS pellets, after which the shear level was lowered to 1000 rpm.
3. Polymer blending was continued at 1000 rpm for a total of 2 hrs.
4. Temperature was dropped to about 182° C. at a 150 rpm at which point the sulfur cross linker was added.
5. Blending was continued at 182° C. and 150 rpm for 2 hrs.
6. Polymerized binder was placed in an oven at 150° C. for approximately 12-15 hrs (overnight) to achieve full swelling of the polymer.

Example 12: Rejuvenation of Highly Aged Asphalt Binder Using the Oil of Example #3

Figure 1:
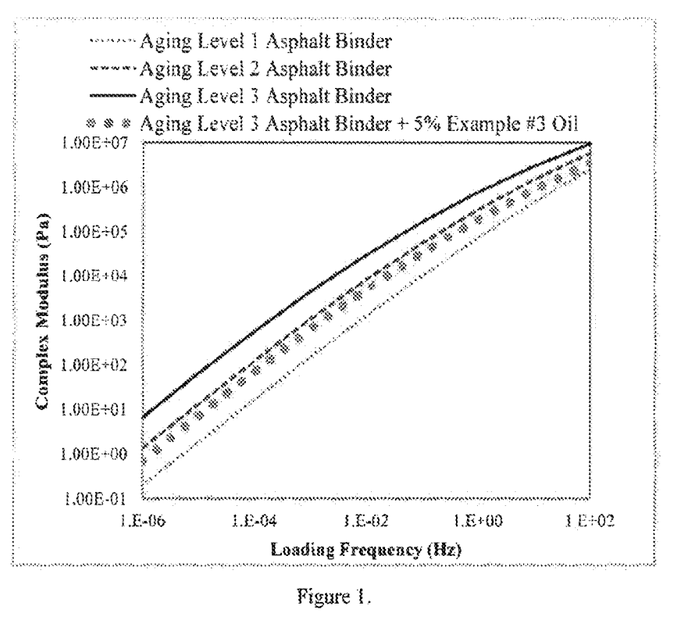
FIGS. 1 and 2 show a complex modulus curve of asphalt as a function of reduced loading frequency.

The example shown in FIG. 1 shows a complex modulus (G*) curve of asphalt as a function of reduced loading frequency, measured using a Dynamic Shear Rheometer (DSR) following ASTM D7175. The measurements were made for samples of the asphalt binder used in Example #3 (PG 64-22) after laboratory aging to three levels:

Aging Level 1: 85 minutes of oxidative aging in Rolling Thin Film Oven at 163° C. (following ASTM D2872).

Aging Level 2: Continued aging of samples after aging level 1 by subjecting it to 20 hrs of oxidative aging at 2.1 MPa air pressure at 100° C. using a Pressure Aging Vessel (following ASTM D6521). According to the Performance Grading specification, 20 hrs of PAV aging accelerates the simulated aging that would normally occur during the performance life of an asphalt pavement.

Aging Level 3: Continued aging of samples after aging level 1 and 2 by subjecting it to an additional 20 hrs of oxidative aging using a Pressure Aging Vessel (PAV) for a total of 40 hrs of PAV aging, representing the aging level of a binder from a severely aged pavement.

FIG. 1 shows that additional aging from level 1 to level 2, and level 2 to level 3 caused significant increase in complex modulus across the reduced frequency spectrum.

The asphalt binder at Aging Level 3 was "rejuvenated" by heating the binder to 150° C. for 1 hr and blending in 5% by weight of the total binder of the Example #3 oil. The curve corresponding to the rejuvenated binder in FIG. 1 shows that the rejuvenation significantly decreased the G* of the aged asphalt across the whole spectrum of reduced frequencies, resulting in a binder with the theological properties of a significantly lower aged asphalt binder.

Example 13: Rejuvenation of Highly Aged Asphalt Binder Using the Oil of Example #4

The example shown in FIG. 1 shows a complex modulus (G*) curve of asphalt as a function of reduced loading frequency, measured using a Dynamic Shear Rheometer (DSR) following ASTM D7175. The measurements were made for samples of the asphalt binder used in Example #3 (PG 64-22) after laboratory aging to three levels described in Example 12, as before, showing that additional aging caused significant increase in complex modulus across the reduced frequency spectrum.

Figure 2:
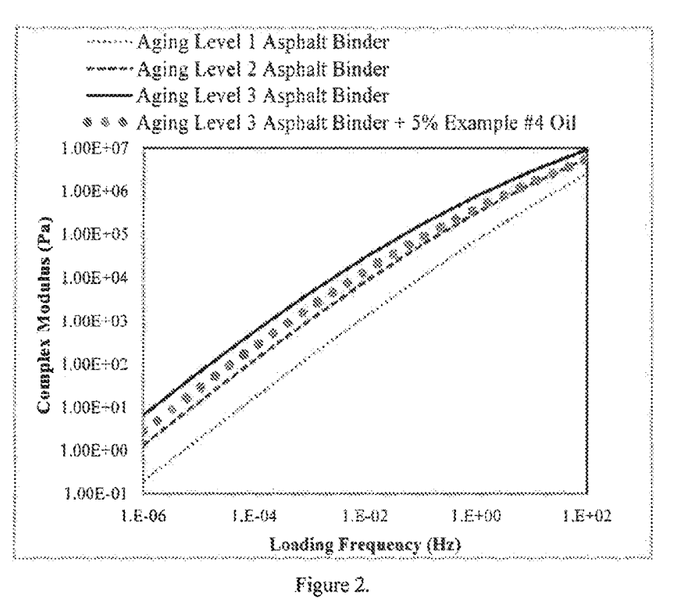

The asphalt binder at Aging Level 3 was "rejuvenated" by heating the binder to 150° C. for 1 and blending in 5% by weight of the total binder of the Example #4 oil. The curve corresponding to the rejuvenated binder in FIG. 2 shows that the rejuvenation significantly decreased the G* of the aged asphalt across the whole spectrum of reduced frequencies, resulting in a binder with the rheological properties of a lower aged asphalt binder.

Example 14: Effect of Sulfurized Oil on Glass Transition

The low temperature performance of asphalt has been shown to be significantly affected by the glass transition temperature of the asphalt, that will occur in the mage of the performance temperature often experienced in the winter (approximately −5 to −40° C.). Furthermore, the rate of asphalt physical hardening has also been shown to be closely associated with glass transition of the asphalt, with the highest rate occurring at the Tg. Thus it is desirable to have a low glass transition temperature to reduce the likelihood that asphalt will reach its glass transition during its performance life. Aging has been known to increase the glass transition temperature of asphalt, thus a desirable attribute of an effective rejuvenator would be to lower the glass transition of the aged asphalt once incorporated.

The first measurement was made for a sample of a PG 64-22 asphalt binder after significant laboratory aging. The laboratory aging consisted of 85 minutes of oxidative aging in Rolling Thin Film Oven at 163° C. (ASTM D2872) followed by 40 hrs of oxidative aging at 2.1 MPa air pressure at 100° C. using a Pressure Aging Vessel (following ASTM D6521), representing the aging level of a binder from a severely aged pavement. The sample is labeled "Aged Asphalt" in FIG. 1.

The second sample, labeled "Aged Asphalt+Polymerized Oil" consisted of:
  95% by weight of the aforementioned PG 58-28 neat binder
  5% by weight of of sulfurized recovered corn oil (RCO) reacted with 1.5% by weight of elemental sulfur at 160° C. for 7 hrs under a Nitrogen sparge. This resulted in a modifier with 16.0% oligomers and a PDI of approximately 1.50.

Figure 3:
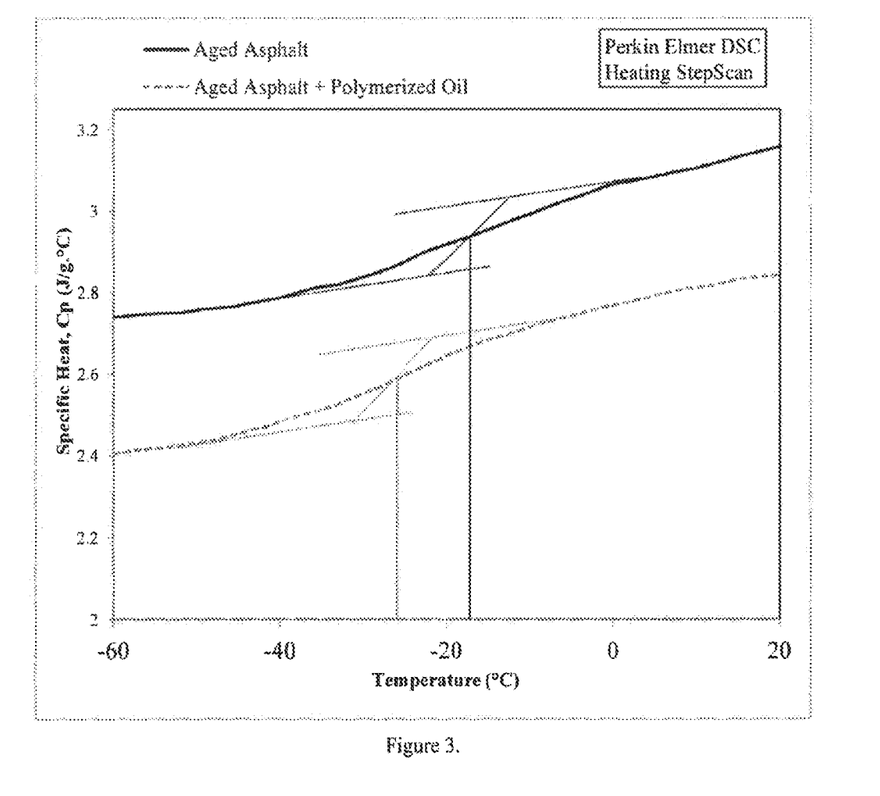
FIG. 3 illustrates a comparison of the DSC specific heat curves.

Thermal analysis of binders before and after rejuvenation using the polymerized oil show that the modifier significantly shifted the Tg of the aged asphalt towards lower temperatures, as shown in Table 12. A comparison of the DSC specific heat curves is shown in FIG. 3.

TABLE 12

| Material Description | Glass Transition Temperature (° C.) |
| --- | --- |
| Aged Asphalt | −17 |
| Aged Asphalt + Polymerized Oil | −27 |

The invention claimed is:

1. A polymerized oil comprising:
a biorenewable, previously modified, or functionalized oil crosslinked with a sulfur-containing compound and having
(a) a polymeric distribution having about 2 to about 80 wt % oligomer content;
(b) a polydispersity index ranging from about 1.30 to about 2.20; and
(c) sulfur content ranging from 0.001 wt % to about 8 wt %.

2. The polymerized oil of claim 1, wherein the polymeric distribution has about 15 to about 60 wt % oligomer content.

3. The polymerized oil of claim 1, wherein the polydispersity index ranges from about 1.50 to about 2.05.

4. The polymerized oil of claim 1, wherein the sulfur content is less than about 6 wt %.

5. The polymerized oil of claim 1, wherein the sulfur content is less than about 4 wt %.

6. The polymerized oil of claim 1, wherein the sulfur content is less than about 2 wt %.

7. The polymerized oil of claim 1, having a flash point ranging from about 100° C. to about 400° C.

8. The polymerized oil of claim 1, having a flash point ranging from about 200° C. to about 350° C.

9. The polymerized oil of claim 1, having a flash point ranging from about 245° C. to about 275° C.

10. The polymerized oil of claim 1, wherein the biorenewable, previously modified, or functionalized oil is selected from the group consisting of palm oil, sunflower oil, corn oil, soybean oil, canola oil, rapeseed oil, linseed oil, tung oil, castor oil, tall oil, cottonseed oil, peanut oil, safflower oil, corn stillage oil, and combinations and crude streams thereof.

11. The polymerized oil of claim 1, wherein the biorenewable, previously modified, or functionalized oil comprises an alkyl ester.

12. The polymerized oil of claim 11, wherein the biorenewable, previously modified, or functionalized oil is selected from the group consisting of methyl, ethyl, propyl, and butyl esters, and combinations thereof.

13. The polymerized oil of claim 1, wherein the biorenewable, previously modified, or functionalized oil has been previously modified.

14. The polymerized oil of claim 1, wherein the biorenewable, previously modified, or functionalized oil is selected from the group consisting of triacylglycerides, diacylglycerides, monoacylglycerides, and combinations thereof.

15. The polymerized oil of claim 1, wherein the sulfur-containing compound is elemental sulfur.

16. The polymerized oil of claim 15, wherein the crosslinking comprises heating to about 130° C. to about 250° C.

17. The polymerized oil of claim 15, wherein the crosslinking comprises heating to about 130° C. to about 220° C.

18. The polymerized oil of claim 15, wherein the crosslinking comprises heating to about 160° C. to about 200° C.

19. The polymerized oil of claim 1, wherein the sulfur content is 0.01 wt % to 8 wt %.

20. A modified asphalt comprising the polymerized oil of claim 1.

21. A rejuvenator for use in asphalt comprising the polymerized oil of claim 1.

22. A modified asphalt, comprising:
(a) about 60 to about 99.9 wt % asphalt binder; and
(b) about 0.1 to about 40 wt % polymerized oil crosslinked with a sulfur-containing compound and comprising
i. a polymeric distribution having about 2 to about 80 wt % oligomer content;
ii. a polydispersity index ranging from about 1.30 to about 2.20; and
iii. sulfur content less than about 8 wt %.

23. The modified asphalt of claim 22, wherein the asphalt binder is for paving applications.

24. A method of incorporating a polymerized oil in asphalt applications, comprising:
  (a) obtaining a polymerized oil crosslinked with a sulfur-containing compound, the polymerized oil comprising:
    i. a polymeric distribution having about 2 to about 80 wt % oligomer content;
    ii. a polydispersity index ranging from about 1.30 to about 2.20; and
    iii. sulfur content less than about 8 wt %; and
  (b) adding the polymerized oil to treat reclaimed asphalt pavement millings (RAP) to be reused in asphalt pavements, thereby obtaining a modified asphalt; wherein the amount of the polymerized oil ranges from 0.1 to 40 wt % of the modified and rejuvenated asphalt.

25. The method of claim 24, further comprising blending the treated reclaimed asphalt pavement millings with bitumen.

* * * * *

UNITED STATES PATENT AND TRADEMARK OFFICE
CERTIFICATE OF CORRECTION

| | | |
|---|---|---|
| PATENT NO. | : 10,316,189 B2 | |
| APPLICATION NO. | : 15/715665 | |
| DATED | : June 11, 2019 | |
| INVENTOR(S) | : Todd L. Kurth et al. | |

It is certified that error appears in the above-identified patent and that said Letters Patent is hereby corrected as shown below:

On the Title Page

On Page 2, item (56) in Column 2, Line 3, delete "White" and insert -- White et al. --, therefor.

In the Specification

In Column 2, Line 20, delete "in" and insert -- an --, therefor.

In Column 2, Line 65, after "such", insert -- as --.

In Column 3, Line 28, delete "oil" and insert -- oils --, therefor.

In Column 3, Line 34, delete "interestified," and insert -- interesterified, --, therefor.

In Column 4, Line 31, delete "bat" and insert -- but --, therefor.

In Column 4, Line 44, delete "Use" and insert -- The --, therefor.

In Column 7, Line 11, delete "daring" and insert -- during --, therefor.

In Column 7, Line 47, delete "cars" and insert -- can --, therefor.

In Column 7, Line 65, delete "suitor" and insert -- sulfur --, therefor.

In Column 8, Line 24, delete "reset" and insert -- met --, therefor.

In Column 11, Line 14, delete "0°" and insert -- 0.1° --, therefor.

In Column 11, Line 48, delete "0°" and insert -- 0.8° --, therefor.

Signed and Sealed this
First Day of October, 2019

Andrei Iancu
*Director of the United States Patent and Trademark Office*

CERTIFICATE OF CORRECTION (continued)
U.S. Pat. No. 10,316,189 B2

In Column 12, Line 3, delete "weighs" and insert -- weight --, therefor.

In Column 12, Line 7, delete "Use" and insert -- The --, therefor.

In Column 12, Line 11, delete "nest" and insert -- neat --, therefor.

In Column 12, Line 38, after "content", insert -- , --.

In Column 13, Line 43, delete "54.88" and insert -- 64.88 --, therefor.

In Column 15, Line 20, delete "mage" and insert -- range --, therefor.